US012622660B2

(12) United States Patent
Pfister

(10) Patent No.: US 12,622,660 B2
(45) Date of Patent: May 12, 2026

(54) DETERMINING A LENGTH OF A STENT

(71) Applicant: Siemens Healthineers AG, Forchheim (DE)

(72) Inventor: Marcus Pfister, Bubenreuth (DE)

(73) Assignee: Siemens Healthineers AG, Forchheim (DE)

(*) Notice: Subject to any disclaimer, the term of this patent is extended or adjusted under 35 U.S.C. 154(b) by 2 days.

(21) Appl. No.: 18/828,299

(22) Filed: Sep. 9, 2024

(65) Prior Publication Data

US 2025/0090115 A1     Mar. 20, 2025

(30) Foreign Application Priority Data

Sep. 15, 2023     (EP) ..................................... 23197566

(51) Int. Cl.
   *A61B 6/40*      (2024.01)
   *A61B 6/00*      (2024.01)
   *A61B 6/50*      (2024.01)
(52) U.S. Cl.
   CPC ............ *A61B 6/4057* (2013.01); *A61B 6/504* (2013.01); *A61B 6/5205* (2013.01)
(58) Field of Classification Search
   CPC ..... A61B 6/4057; A61B 6/504; A61B 6/5205; A61B 5/1076; G06T 7/62
   See application file for complete search history.

(56) References Cited

U.S. PATENT DOCUMENTS

| | | |
|---|---|---|
| 2009/0088830 A1 | 4/2009 | Mohamed |
| 2011/0235876 A1 | 9/2011 | Pfister et al. |
| 2014/0111541 A1 | 4/2014 | Tolkowsky |
| 2015/0094567 A1 | 4/2015 | Pfister |
| 2016/0022208 A1* | 1/2016 | Gopinath ........... A61B 5/02154 600/427 |
| 2020/0188027 A1 | 6/2020 | Sakuragi |

FOREIGN PATENT DOCUMENTS

| | | |
|---|---|---|
| DE | 102010012621 A1 | 9/2011 |
| DE | 102013205537 A1 | 3/2014 |
| DE | 102013219737 B4 | 5/2019 |

OTHER PUBLICATIONS

Koutouzi, Giasemi, et al. "Iliac artery deformation during EVAR." Vascular 27.5 (2019): 511-517 (Abstract).
Mohammadi, Hossein, et al. "A numerical preoperative planning model to predict arterial deformations in endovascular aortic aneurysm repair." Annals of biomedical engineering 46 (2018): 2148-2161.

* cited by examiner

*Primary Examiner* — Peter Luong
(74) *Attorney, Agent, or Firm* — Lempia Summerfield Katz LLC

(57)     ABSTRACT

The length of a stent for a branched vessel may be determined without a contrast agent if possible. To this end, a method includes: acquiring a projection recording of the vessel into which an instrument has been introduced; determining the instrument in the projection recording; estimating a 3D reconstruction of the determined instrument from the projection recording in order to obtain a virtual 3D instrument; establishing a start point and an end point on the virtual 3D instrument with reference to an overlay of the virtual 3D instrument and the projection recording; and automatically determining a distance between the start point and the end point along the virtual 3D instrument as the length for the stent.

17 Claims, 4 Drawing Sheets

DETERMINING A LENGTH OF A STENT

The present patent document claims the benefit of European Patent Application No. 23197566.5, filed Sep. 15, 2023, which is hereby incorporated by reference in its entirety.

TECHNICAL FIELD

The present disclosure relates to a method for determining a length for a stent for a branched vessel. The present disclosure further relates to a corresponding arrangement for determining the length. Furthermore, the present disclosure also relates to a corresponding computer program.

BACKGROUND

An abdominal aortic aneurysm (AAA) is a vascular dilation of the abdominal aorta. Such an AAA is treated by inserting various stent grafts (e.g., composite vascular stents). Guide wires and catheters are inserted into the aorta via both groins and are then used to insert a main (aortic) stent onto which stents for the femoral arteries (iliaca) are then "flange-mounted" (see, e.g., FIG. 3). In the case of more complex stents, known as fenestrated (having windows) or branched stents, further part stents are added. In order not to have to inject contrast agent for the continuous display of vessels for control purposes during the complex stent positioning, a reference image that shows the vessels (e.g., the aorta and vessels branching off the aorta) may be overlaid (e.g., in an anatomically correct manner) as a positioning aid (see, e.g., FIG. 4).

A significant problem consists in determining the length of the iliac stents to be flange-mounted. This length may only be partly determined before the operation, even using a pre-segmented and measured data set. Although the length of the individual vessels may be known, (for example, as length of the center lines), the subsequent position of the femoral openings of the aortic stent that has been inserted is not known, and this is known only during the intervention (after depositing the stent), because the vessel is deformed by the stent that is inserted. In addition, the iliac arteries become significantly shorter as a result of the insertion of the rigid instruments (and stents). For example, measurements show that the deformation causes the length of the iliaca to be shortened from 66±12 mm preoperationally to 60±9 mm intra-operationally, (e.g., 6 mm on average). This shortening remains thereafter.

In order to allow for both effects, it is standard practice, after inserting an aortic stent and probing the femoral opening with a (rigid) guide wire, to perform an angiography using a special angio-catheter with markings at 1-cm intervals. On the basis of "counting" the markings between iliac bifurcation (iliac fork) and bifurcation of the aortic stent that has been inserted, the length of the required iliac stent is then determined.

In the publication DE 10 2013 219 737 B4, an angiographic examination method for depicting a target region inside a patient with a vascular system is developed in such a way that a three-dimensional correction facility is possible from just one projection image, thereby considerably improving the method sequence and radiation exposure for the patient. To this end an examination method is proposed having acts as follows:

In act S1, a volume data set of the target region is acquired with the examination object. In act S2, the volume data set to the C-arm is registered. In act S3, information is extracted about an assumed course of the examination object in the volume data set inside the target region. In act S4, at least one 2D projection image of a medical instrument inserted in the target region is generated, which has a deviation between overlay and actually projected instrument. In act S5, the at least one 2D projection image and the registered volume data set are 2D/3D merged for generating a 2D overlay image. In act S6, the instrument inserted in the target region in the 2D overlay image is detected with a first projection matrix. In act S7, a virtual 2D projection is generated using a virtual projection matrix. In act S8, the instrument is 3D reconstructed, whereby a 3D position of the instrument is determined from the two projections. In act S9, the 2D projection image is overlayed with the virtual 2D projection, and at least one part of the 2D projection image is distorted such that the current and the assumed course of the vessels are brought into congruence. Using this approach, it is possible to perform the 3D reconstruction of rigid wires in 3D from a projection.

The publication DE 10 2010 012 621 A1 describes an estimation method for determining a contour of a vessel which has been deformed for example by a rigid instrument (for example, guide wire).

SUMMARY AND DESCRIPTION

The object of the present disclosure is therefore to determine the length of a stent that is to be inserted and thereby to minimize the exposure of an object or patient to radiation or contrast agents.

The scope of the present disclosure is defined solely by the appended claims and is not affected to any degree by the statements within this summary. The present embodiments may obviate one or more of the drawbacks or limitations in the related art.

According to the disclosure, a method for determining a length for a first stent for a branched vessel is provided. For example, a stent graft is to be inserted into the abdominal aorta at the iliac fork (bifurcation). In this case, for example, a stent (referred to as a second stent in the present document) is already inserted in the aorta and the cited first stent is added for at least one femoral artery. Both stents are connected together. In order to provide that the first stent does not, for example, cover a distal branching in the femoral artery, it only has a specific length. The length of the first stent is determined for this purpose.

In order to achieve this, the method includes acquiring a projection recording of the vessel into which an (elongated) instrument (for example, catheter, guide wire) has been introduced. The projection recording may be a radioscopy image that is obtained using x-radiation. The projection recording may however also be obtained by other radioscopic techniques, (e.g., sonography, etc.). The recording may be made from a specific direction.

This is followed by determining (which may include or mean automatically identifying) the instrument in the projection recording. For example, the instrument may be a catheter that is automatically identified by correspondingly suitable image processing. In particular, the shape and extent thereof may be registered. The type of instrument (for example, guide wire) may also be identified if applicable. The instrument may however also be determined for example by setting markers (e.g., using a detection device).

In a further act, a 3D reconstruction of the instrument that has been determined or automatically identified is performed or estimated on the basis of the projection recording in order to obtain a virtual 3D instrument. The shape of the instrument that has been determined or identified is therefore reconstructed three-dimensionally. The (2D) projection recording is used as a basis for this. If applicable, one or more additional data sets (for example, volume data set of the vessel) may also be used for the 3D reconstruction of the determined instrument. A single projection recording of the vessel with the instrument that has been introduced may be sufficient. The 3D reconstruction results in a virtual 3D instrument in its three-dimensional form.

In a further act, a start point and an end point on the virtual 3D instrument are established by overlaying the 3D instrument and the projection recording. The real (2D) projection recording, and the virtual 3D instrument are therefore overlaid. The projection recording may show further details of the vessel, such as a previously inserted second stent, a fork, a branch, etc. These details or additional information may be used to establish the start point and the end point on the virtual 3D instrument. For example, a distal opening of the second stent may be used as a start point and an iliac bifurcation (e.g., set, 5.50) may be used as the end point in order to determine the length.

Lastly, the method provides for automatically determining a distance between the start point and the end point along the virtual 3D instrument as the length for the first stent. For example, the virtual 3D instrument is a virtual measuring catheter, e.g., which has the rigidity of a stent. Using the established start point and end point on the virtual 3D instrument, the length along the virtual structure may be calculated automatically. A physician may use this length to calculate the actual length of a stent that is inserted. For example, for the first stent, the physician may use precisely the length that was automatically determined. However, if the physician wants the first and second stent to overlap, the physician adds a corresponding overlap quantity to the automatically determined length in order to arrive at the length that is actually desired for the first stent.

This means that, instead of using an actual image with a measuring catheter, it is advantageously possible to use a recording with a virtual 3D instrument in order to determine the length of a stent that is to be inserted. It is thereby possible to reduce the patient exposure to contrast agents and radiation.

In an embodiment, the start point on the virtual 3D instrument is established at an automatically identified opening of a second stent. As explained above, the second stent may be an aortic stent. The aortic stent may have a tubular main body to which short limbs for the femoral arteries are distally attached. Iliac stents are then patched onto the two limbs. For example, the iliac stents have a standard length of 60, 80, or 100 mm. Using the length measurement, it is possible to select the appropriate iliac stent, e.g., allowing for an overlap of the two stents of 1 to 2 cm. The automatic identification of the opening (e.g., limb opening) of the second stent may be effected by image recognition software, which may identify an ellipse of the round opening in the projection.

In a further embodiment, the end point on the virtual 3D instrument is established on the basis of an automatically identified branching of the vessel in the projection recording or in a 3D contour of the vessel that is overlaid on the projection recording. For example, this or other image processing software may also simply identify a fork of the vessel (for example, iliac bifurcation) of the femoral artery in the 2D projection recording and therefore establish the location of this iliac bifurcation as the end point. In some cases, it may be more beneficial for the branching in the 3D contour of the vessel (which is sometimes deformed by the instrument) to be identified automatically.

In an advantageous embodiment of the method, the start point or the end point may be established by manually marking one or two corresponding positions. For example, a corresponding start point and/or end point is manually marked on the projection image and registered (e.g., automatically registered). It is thereby possible, for example, by clicking on a corresponding position in a graphical representation to establish a position of the start point or end point. In some cases, the marked positions may also be manually moved. In some cases, automatically established start and end points may also be manually corrected.

In another embodiment, only the projection recording is used for the purpose of performing the 3D reconstruction of the instrument that is (manually or automatically) determined or automatically identified in the projection recording, in order to obtain the virtual 3D instrument. In this case, the three-dimensional form of the instrument may be estimated from the (2D) projection recording. For the purpose of the 3D reconstruction, the method that is cited in the introduction in connection with the publication DE 10 2013 219 737 B4 may be used, (i.e., the proposed acts S1 to S9 may therefore be performed for the reconstruction).

In a further embodiment, the instrument is a catheter, (e.g., an angio-catheter), or a guide wire. The instrument that is recorded by the projection recording may therefore be a standard catheter, for example. In particular, it does not have to be a gold measuring catheter.

In a further embodiment, the virtual 3D instrument represents a virtual measuring catheter with measurement markings. This means that the virtual measuring catheter, like a real measuring catheter, may have measurement markings on the basis of which the physician may estimate a corresponding length. Moreover, the measurement markings also show the physician any three-dimensional deformations in a two-dimensional projection recording, specifically if the measurement markings are closer together than at other positions.

In a specific embodiment, the vessel contains a femoral artery, the second stent is an aortic stent in an abdominal aorta, and the branching is an iliac bifurcation. Therefore, as already mentioned in the example above, the first stent is inserted into a femoral artery. The first stent is intended to start at the aortic stent in the abdominal aorta and to end before the iliac bifurcation. An abdominal aortic aneurysm may be treated using such a composite vascular stent.

In an alternative embodiment, the first stent is an intracranial stent. The method may therefore be used not only for iliac stents but also for stents inside the brain or other organs. Lengths of stents are estimated here likewise in order to establish their total lengths or distances to fenestrations, for example.

The method may therefore be used in an embodiment not only to determine the total length of a stent that is to be inserted, but also to determine a distance to a stent opening or between two stent openings. For this purpose, the method for the length of the first stent is a distance from an opening to a window or a distance between two windows of the first stent. This means that stents for renal arteries may also be dimensioned more easily, in particular with regard to their fenestrations.

In a further embodiment, a deformation of the vessel by the instrument is modeled and for the start point and/or end point to be established on this basis. This means that the vessel is deformed by the instrument situated therein and the deformed vessel is modeled. The modeling may take place in a volume data set, for example. The modeled deformed vessel may then be used in combination with the 2D projection recording to establish the start point or end point for determining the length. The start point and end point may be determined more reliably using the deformed vascular model.

In a further embodiment, the second stent has a marking at the opening, and the opening of the second stent is automatically identified with the aid of the marking. For example, at both limb openings, the aortic stent has markings which may be identified easily in the x-ray image. For example, the start point for the length of the first stent may be established more easily thereby. Particular advantages are derived if such a marking is identified automatically, and the corresponding position may also be established automatically.

According to a further embodiment, the second stent has a 3D marker, with reference to which the opening or a bifurcation of the second stent may be localized in three dimensions. For example, the 3D marker is arranged at the bifurcation of the second stent. By this arrangement, the openings of the limbs are easier to locate in the projection recording, such that it is also possible thereby to determine or automatically identify the opening(s) if applicable.

The object cited above is also achieved by an arrangement for determining a length for a first stent for a branched vessel. The arrangement or system includes: an acquisition device configured to acquire a projection recording of the vessel into which an (elongated) instrument has been introduced; a detection device configured to determine the instrument in the projection recording; a computing device configured to estimate (or perform) a 3D reconstruction of the determined (for example, automatically identified) instrument from the projection recording in order to obtain a virtual 3D instrument; and a determining device configured to establish a start point and an end point on the virtual 3D instrument with reference to an overlay of the virtual 3D instrument and the projection recording, wherein the computing device is also configured to automatically determine a distance between the start point and the end point along the virtual 3D instrument as the length for the first stent.

The acquisition device may use x-ray technology or be based on MRT or sonography, for example. The detection device may use an image recognition algorithm, this being implemented on a computer or a computing device with a processor, for the automatic identification. The arrangement may also use a computing device for the 3D reconstruction. The detection device may be integrated into the computing device. The determining device may likewise be integrated into the computing device as far as automatic determination of start point and end point is possible. Alternatively, the determining device may also include a user interface by which a user may set or mark start and end points.

The present disclosure further relates to a computer program including instructions that, when executed in a processor of the arrangement cited above, cause the arrangement to execute the method described above.

With regard to use cases or application scenarios that may arise in the context of the method and are not explicitly described here, the method may include outputting an error message and/or a request for input of a user response, and/or selecting a default setting and/or a predefined initial state.

BRIEF DESCRIPTION OF THE DRAWINGS

The present disclosure is now explained in greater detail with reference to the appended drawings, in which:

6

Figure 1:
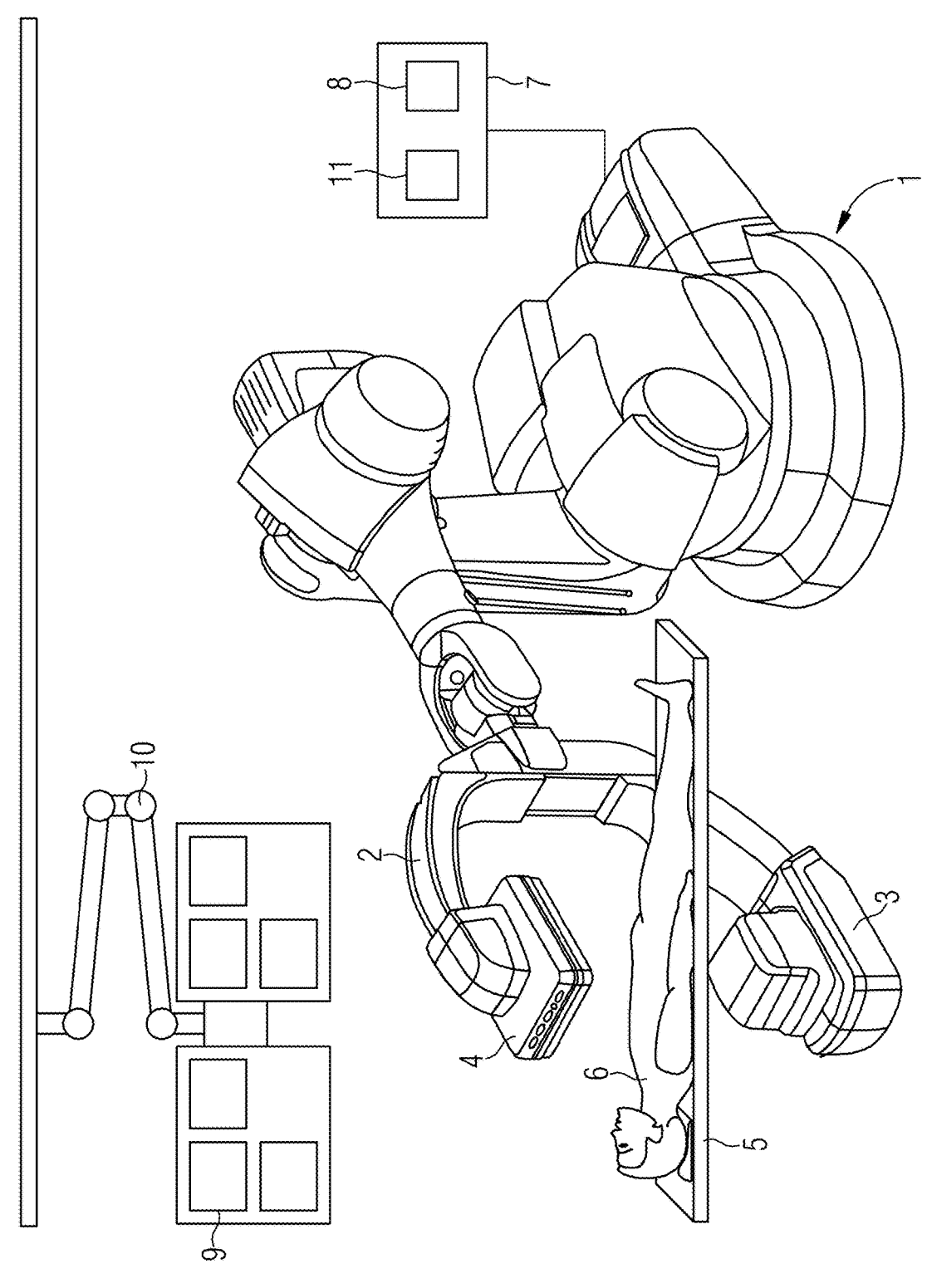

FIG. 1 depicts a C-arm angiography system with an industrial robot as a supporting apparatus.

Figure 2:
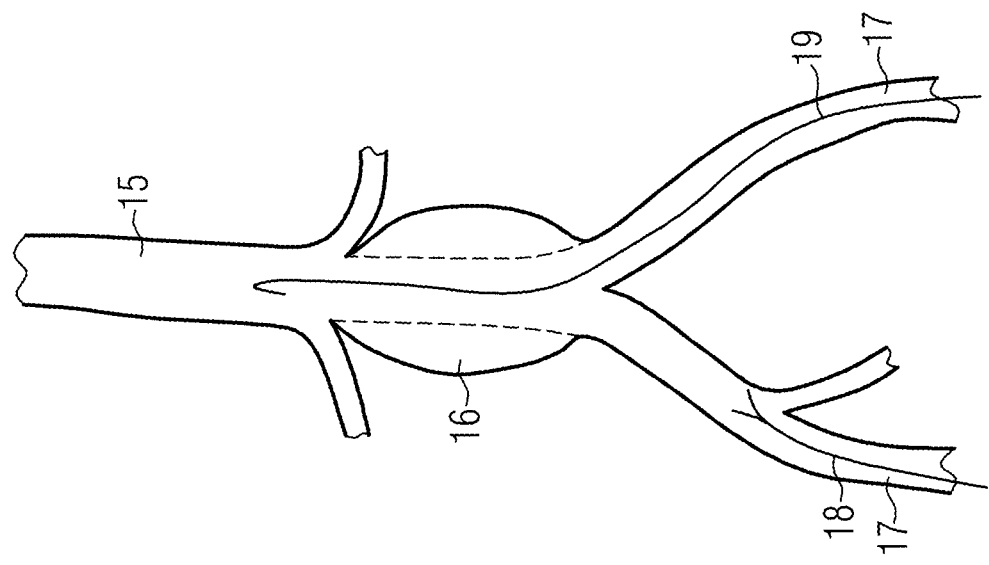

FIG. 2 depicts an example of an abdominal aorta with an aortic aneurism.

Figure 3:
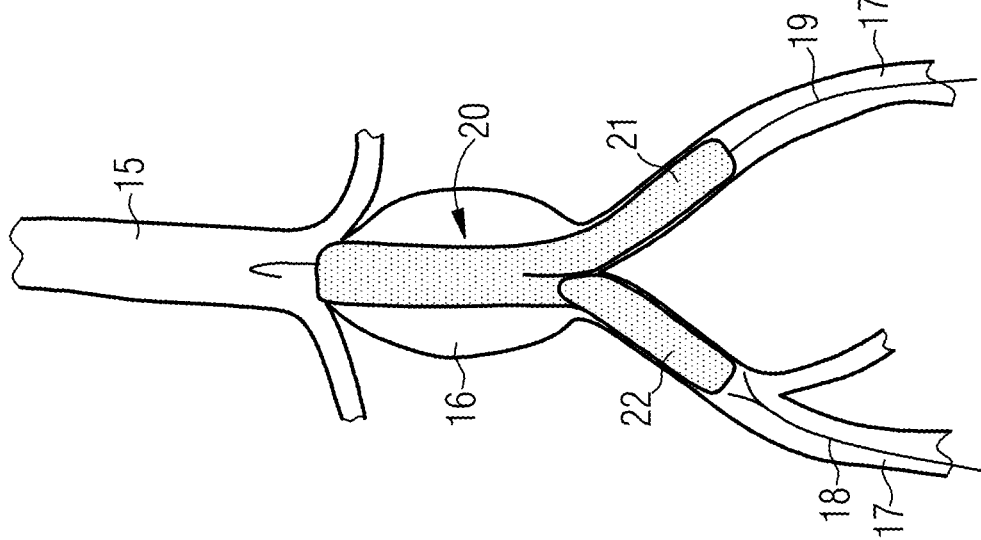

FIG. 3 depicts the aorta as per FIG. 2 with a stent graft that has been introduced.

Figure 4:
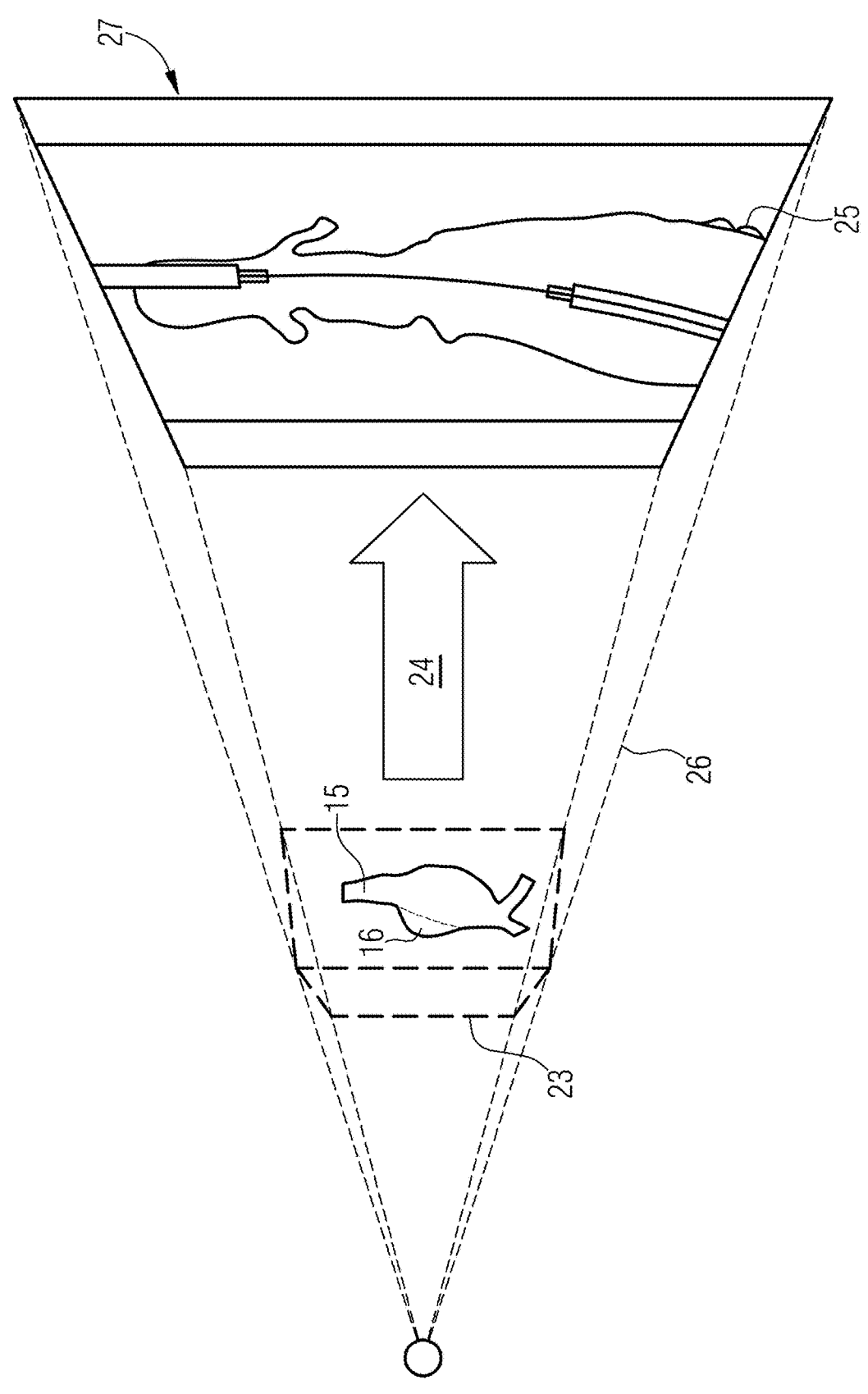

FIG. 4 depicts an example of a diagram to illustrate the principle of a 2D-3D overlay.

Figures 5, 6:
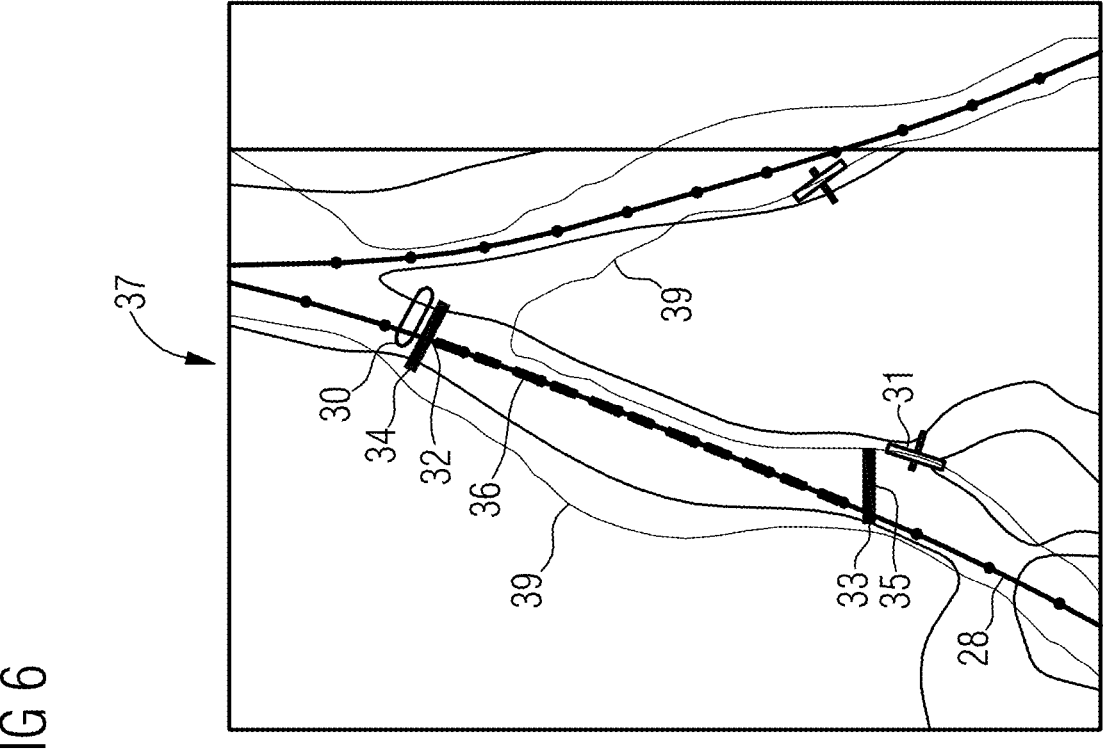

FIG. 5 depicts an example of an automatic identification of a wire that has been inserted and the 3D reconstruction thereof.

FIG. 6 depicts an example of an establishment of start point and end point for automatic determination of the length.

DETAILED DESCRIPTION

By way of example, FIG. 1 shows a mono-planar x-ray system including a C-arm 2 which is held on a stand 1 in the form of an industrial or folding-arm robot with six axes, at the ends of which C-arm 2 are attached an x-ray source, for example an x-ray emitter 3 including x-ray tubes and collimators, and an x-ray image detector 4 as an image recording unit. The realization of the x-ray diagnostic facility is not dependent on the industrial robot. Conventional C-arm devices may also be used.

Situated in the beam path of the x-ray emitter 3 on a table plate 5 of a patient support table is a patient 6 to be examined or a technical item as an examination object. Attached to the x-ray diagnostic facility is a system control unit 7 including a computing device 8 for obtaining a virtual 3D instrument, which receives and processes the image signals from the x-ray image detector 4 (operating elements are not shown, for example).

The x-ray images may then be observed on displays in a bank of monitors 9. The bank of monitors 9 may be held by a ceiling-mounted and linearly-mobile support system 10 which provides tilt, swivel and height adjustment and includes an extension arm and lowering bracket. Also provided in the system control unit 7 is a determining device 11 for establishing a start point and an end point on the virtual 3D instrument.

FIG. 2 illustrates an abdominal aorta 15 that has an abdominal aortic aneurysm (AAA) 16. An abdominal aortic aneurysm (AAA) 16 is a vascular dilation on the abdominal aorta 15. The aorta 15 branches into the femoral arteries 17 arteria iliaca communis.

The aortic aneurysm 16 is treated by inserting a stent graft, (e.g., a composite vascular stent), as illustrated in FIG. 3. For this purpose, guide wires 18 and catheters 19, by which the stent grafts 20 are inserted, are inserted into the aorta 15 through the femoral arteries 17 by way of both groins.

In the case of complex stent grafts 20 that also include the femoral arteries 17, the final stent may be composed of "part-stents," for example, when an iliac stent 22 is "flange-mounted" via a so-called window (opening) onto an aortic stent 21, this representing a main stent (second stent) that projects through the AAA into one of the femoral arteries 17, as a part-stent (first stent) for the other femoral artery.

In order to provide the physician with additional information to assist with the placement of AAA stents, even today, a previously recorded reference image is overlaid in an anatomically correct manner over a current radioscopy image that was created by a C-arm system 2 to 4. This reference image may be a 3D data set or volume data set of the aorta 15 with the abdominal aortic aneurysm 16 as per FIG. 3, for example a pre-segmented preoperative computed tomography or rotational angiography using a C-arm angiography system.

FIG. 4 shows the overlay of a current radioscopy image with the pre-interventionally generated volume data set 23, which may be present for example in the form of a 3D grating model as depicted by way of example in the cube. The 3D grating model is mapped into the radioscopy image as 2D segmentation 25 by 3D projection 24, as symbolized by the dotted lines 26, and a 2D/3D overlay image 27 is produced as a reference image.

According to an embodiment, an estimation of length is possible for example by combining information from a preoperative (pre-segmented) CT and an intraoperative radioscopy image. To this end, provision is made for obtaining, for example, a 3D data set of the aorta and the iliac vessels, the 3D data set being obtained via CT and registered to the angiography system or C-arm. In addition, this data set may also contain information about vascular branches, in particular the iliaca interna branches. Furthermore, the main or aortic stent (second stent) may be inserted into the aorta. The 3D data set may therefore come for example from preoperative (registered to the C arm) CT or MR angiography or also intraoperative 3D imaging.

The workflow described below may be used to determine the stent length of the first stent (part stent). The determining of the stent length may be effected in particular without contrast agents and intraoperatively. The workflow includes the following acts.

In act 1, a radioscopy image (projection recording) is recorded from the projection direction identified by the physician (background of FIG. 5).

In act 2, the wire 18 that has been inserted into the femoral artery 17 is automatically identified in the radioscopy image. This may be effected by corresponding image recognition software, for example.

In act 3, 3D reconstruction of the (deformed) instrument is performed. In this 3D reconstruction, a virtual 3D instrument 28 is produced from the (2D) projection or projection recording. This 3D reconstruction may be effected in accordance with the publication DE 10 2013 219 737 B4 cited in the introduction. In particular, acts S1 to S9 may be used for this purpose. For example, the virtual 3D instrument corresponds to a wire which has been deformed by the vessel. If applicable, the virtual 3D instrument (here the virtual 3D wire) is shown as per FIG. 5 with length markings on a monitor. A deformation of the virtual wire 28 in a z-direction (perpendicular to the plane of the image) may be identified because the length markings 29 then lie closer together.

In act 4, an automatic identification of the inserted (second) stent or the distal (i.e., furthest from the heart) opening 30 thereof (see FIG. 6) is performed. Image recognition software may again be used for this automatic identification.

In act 5, an automatic determination of the distance between the automatically identified opening 30 of the (second) stent and a likewise automatically identified bifurcation 31 of the vessel along the (curved) virtual 3D instrument is performed. A start point 32 may be, for example, an intersection point between an estimated cross-sectional line 34 through the vessel at the opening 30, or in the immediate vicinity thereof, and the virtual 3D instrument or wire. An end point 33 may be, for example, an intersection point between a cross-sectional line 35 and the virtual wire 28 at the bifurcation, or in the immediate vicinity thereof. That section 36 of the virtual 3D instrument 28 which is broken-marked in FIG. 6 and represents the length to be determined is shown between start point 32 and end point 33.

In act 6, the radioscopy image or the projection recording 37, 37' may optionally be overlaid with a contour 38 of the vessel, so that the treating physician may navigate more easily.

In FIG. 5, the projection recording 37 is overlaid with the non-deformed contour 38 of the vessel into which the first stent is inserted. It may be seen that the guide wire 18 runs partially outside the contour 38 of the vessel. This is because the vascular deformation produced by the guide wire 18 is not taken into consideration in the contour 38. In order to allow greater ease of navigation for the physician, the deformation of the vessel may therefore be estimated. If the contour 39 of the deformed vessel is now overlaid on the projection recording 37 as per FIG. 6, it may be seen that the guide wire 18 or the virtual 3D instrument 28 runs within the contour 39 of the deformed vessel. The estimation of the vascular deformation may be effected in accordance with the publication DE 10 2010 012 621 A1 cited in the introduction. The physician may consequently navigate more easily during the intervention.

In an alternative embodiment, the start point 32 and the end point 33 may also be set by manual marking, for example on the projection recording 37. The manual marking may be effected by "clicking" on the corresponding position in the radioscopy image or the projection recording 37.

In a further embodiment variant, a special marking may also be applied to the aortic stent (second stent) at the bifurcation, which special marking facilitates automatic identification in the 2D image (projection recording 37). In particular, this marking may be applied in the region of the opening 30 (see FIG. 6).

In a further embodiment, a 3D marker may also be applied at the aortic stent (second stent) (for example at the bifurcation), thereby allowing 3D localization of the bifurcation. It is thus possible more precisely to effect an overlay of a 2D projection recording and a 3D reconstruction of the vessel.

According to a further embodiment variant, instead of the distal opening at the stent bifurcation, it is possible to mark or automatically identify any other point which allows the desired length to be calculated. The other point may also lie on the virtual 3D instrument (virtual wire), so that the determination of the length may be suitably effected along the 3D instrument.

The described method is not restricted to the calculation of the length of iliac stents but may be applied correspondingly to the calculation of distances between fenestrations (for example stent for renal arteries) or to the calculation of the length of intracranial stents.

According to the embodiments proposed above, it is possible to determine the length of vascular sections intraoperatively and without contrast agents, in order to calculate corresponding stent lengths.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a length for a first stent for a branched vessel, the method comprising:

acquiring a projection recording of the branched vessel into which an instrument has been introduced;

determining the instrument in the projection recording;

estimating a three-dimensional (3D) reconstruction of the determined instrument from the projection recording in order to obtain a virtual 3D instrument;

establishing a start point and an end point on the virtual 3D instrument with reference to an overlay of the virtual 3D instrument and the projection recording; and automatically determining a distance between the start point and the end point along the virtual 3D instrument as the length for the first stent.

2. The method of claim 1, wherein the start point on the virtual 3D instrument is established with reference to an automatically identified opening of a second stent.

3. The method of claim 2, wherein the end point on the virtual 3D instrument is established with reference to an automatically identified branching of the branched vessel in the projection recording or in a 3D contour that is overlaid on the projection recording.

4. The method of claim 3, wherein the branched vessel comprises a femoral artery, and wherein the second stent is an aortic stent in an abdominal aorta, and wherein the branching is an iliac bifurcation.

5. The method of claim 2, wherein the branched vessel comprises a femoral artery, and wherein the second stent is an aortic stent in an abdominal aorta, and wherein a branching of the branched vessel is an iliac bifurcation.

6. The method of claim 2, wherein the second stent has a marking at the opening, and wherein the opening of the second stent is automatically identified with reference to the marking at the opening.

7. The method of claim 2, wherein the second stent has a 3D marker with reference to which the opening or a bifurcation of the second stent is configured to be localized in three dimensions.

8. The method of claim 1, wherein the end point on the virtual 3D instrument is established with reference to an automatically identified branching of the branched vessel in the projection recording or in a 3D contour that is overlaid on the projection recording.

9. The method of claim 1, wherein the establishing of the start point or the end point is effected by manually marking one or two corresponding positions.

10. The method of claim 1, wherein the projection recording is an only recording used for performing the 3D reconstruction of the determined instrument from the projection recording in order to obtain the virtual 3D instrument.

11. The method of claim 1, wherein the instrument is a catheter or a guide wire.

12. The method of claim 11, wherein the catheter is an angio-catheter.

13. The method of claim 1, wherein the virtual 3D instrument represents a virtual measuring catheter with measurement markings.

14. The method of claim 1, wherein the first stent is an iliac stent or an intracranial stent.

15. The method of claim 1, wherein the length for the first stent is a distance from an opening to a window or a distance between two windows of the first stent.

16. The method of claim 1, wherein a deformation of the branched vessel by the instrument is modeled and the start point and/or the end point are established with reference thereto.

17. An arrangement for determining a length for a first stent for a branched vessel, the arrangement comprising:

an acquisition device configured to acquire a projection recording of the branched vessel into which an instrument has been introduced;

a detection device configured to determine the instrument in the projection recording;

a computing device configured to estimate a three-dimensional (3D) reconstruction of the determined instrument from the projection recording in order to obtain a virtual 3D instrument; and a determining device configured to establish a start point and an end point on the virtual 3D instrument with reference to an overlay of the virtual 3D instrument and the projection recording, wherein the computing device is further configured to automatically determine a distance between the start point and the end point along the virtual 3D instrument as the length for the first stent.

* * * * *